(12) United States Patent
Higgins et al.

(10) Patent No.: US 8,663,146 B2
(45) Date of Patent: *Mar. 4, 2014

(54) ANGIOGENESIS INITIATION AND GROWTH

(75) Inventors: Joel C. Higgins, Claypool, IN (US); Bruce Simon, Mountain Lakes, NJ (US); Jennifer E. Woodell-May, Warsaw, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 131 days.

This patent is subject to a terminal disclaimer.

(21) Appl. No.: 13/234,675

(22) Filed: Sep. 16, 2011

(65) Prior Publication Data

US 2012/0010559 A1     Jan. 12, 2012

Related U.S. Application Data

(63) Continuation of application No. 11/714,520, filed on Mar. 6, 2007, now Pat. No. 8,034,014.

(51) Int. Cl.
| | |
|---|---|
| *A61M 1/00* | (2006.01) |
| *A61M 35/00* | (2006.01) |
| *A61M 37/00* | (2006.01) |
| *A61K 41/00* | (2006.01) |
| *A61K 35/14* | (2006.01) |
| *A61K 35/16* | (2006.01) |
| *A61N 2/02* | (2006.01) |

(52) U.S. Cl.
USPC .......... 604/4.01; 604/5.01; 604/6.15; 604/20; 604/289; 604/290; 604/319; 424/93.1; 424/93.7; 424/93.72

(58) Field of Classification Search
USPC ........ 604/4.01, 5.01, 6.15, 20, 289, 290, 319; 424/93.1, 93.7, 93.72
See application file for complete search history.

(56) References Cited

U.S. PATENT DOCUMENTS

| | | |
|---|---|---|
| 3,871,961 A | 3/1975 | Gianessi |
| 4,467,809 A | 8/1984 | Brighton |
| 4,820,626 A | 4/1989 | Williams et al. |
| 4,846,181 A | 7/1989 | Miller |
| 5,035,708 A | 7/1991 | Alchas et al. |
| 5,131,907 A | 7/1992 | Williams et al. |

(Continued)

FOREIGN PATENT DOCUMENTS

| | | |
|---|---|---|
| EP | 0417818 | 3/1991 |
| EP | 2186877 | 5/2010 |

(Continued)

OTHER PUBLICATIONS

"Stem Cell Basics", National Institutes of Health, http://stemcells.nih.gov/info/basics/basics4.asp. Aug. 12, 2005 (6 pages).

(Continued)

*Primary Examiner* — Adam Marcetich
(74) *Attorney, Agent, or Firm* — Harness, Dickey

(57) ABSTRACT

Methods for promoting angiogenesis comprising administering platelet-rich plasma to a site and stimulating the site with an electromagnetic field. Platelets include platelet-rich plasma and compositions can further include stem cells such as adipose stromal cells and cells derived from bone marrow aspirate. Methods also comprise isolating platelets from a patient's blood, forming a composition including the platelets, delivering the composition to a site in need of treatment, and electrically stimulating the site.

23 Claims, 4 Drawing Sheets

(56) References Cited

U.S. PATENT DOCUMENTS

| | | |
|---|---|---|
| 5,165,938 A | 11/1992 | Knighton |
| 5,197,985 A | 3/1993 | Caplan et al. |
| 5,226,914 A | 7/1993 | Caplan et al. |
| 5,292,252 A | 3/1994 | Nickerson et al. |
| 5,318,782 A | 6/1994 | Weis-Fogh |
| 5,338,286 A | 8/1994 | Abbott et al. |
| 5,486,359 A | 1/1996 | Caplan et al. |
| 5,571,418 A | 11/1996 | Lee et al. |
| 5,585,007 A | 12/1996 | Antanavich et al. |
| 5,599,558 A | 2/1997 | Gordinier et al. |
| 5,641,622 A | 6/1997 | Lake et al. |
| 5,663,051 A | 9/1997 | Vlasselaer |
| 5,707,331 A | 1/1998 | Wells et al. |
| 5,788,662 A | 8/1998 | Antanavich et al. |
| 5,811,094 A | 9/1998 | Caplan |
| 5,814,094 A | 9/1998 | Becker et al. |
| 5,814,295 A | 9/1998 | Martin et al. |
| 5,824,084 A | 10/1998 | Muschler |
| 5,842,477 A | 12/1998 | Naughton |
| 5,906,934 A | 5/1999 | Grande et al. |
| 5,916,743 A | 6/1999 | Lake et al. |
| 5,919,679 A | 7/1999 | Blackman et al. |
| 6,054,122 A | 4/2000 | MacPhee et al. |
| 6,063,297 A | 5/2000 | Antanavich et al. |
| 6,117,425 A | 9/2000 | MacPhee et al. |
| 6,200,606 B1 | 3/2001 | Peterson et al. |
| 6,214,223 B1 | 4/2001 | Ohkawa |
| 6,214,338 B1 | 4/2001 | Antanavich et al. |
| 6,214,369 B1 | 4/2001 | Grande et al. |
| 6,235,251 B1 | 5/2001 | Davidson |
| 6,316,247 B1 | 11/2001 | Katz et al. |
| 6,322,785 B1 | 11/2001 | Landesberg et al. |
| 6,323,146 B1 | 11/2001 | Pugh et al. |
| 6,353,763 B1 | 3/2002 | George et al. |
| 6,355,239 B1 | 3/2002 | Bruder et al. |
| 6,387,367 B1 | 5/2002 | Davis-Sproul et al. |
| 6,398,972 B1 | 6/2002 | Blasetti et al. |
| 6,429,013 B1 | 8/2002 | Halvorsen et al. |
| 6,432,119 B1 | 8/2002 | Saadat |
| 6,485,963 B1 | 11/2002 | Wolf et al. |
| 6,541,024 B1 | 4/2003 | Kadiyala et al. |
| 6,569,654 B2 | 5/2003 | Shastri et al. |
| 6,585,992 B2 | 7/2003 | Pugh et al. |
| 6,605,275 B1 | 8/2003 | Boyse et al. |
| 6,623,472 B1 | 9/2003 | Reinecke et al. |
| 6,623,959 B2 | 9/2003 | Harris |
| 6,649,072 B2 | 11/2003 | Brandt et al. |
| 6,652,473 B2 | 11/2003 | Kaufman et al. |
| 6,673,597 B2 | 1/2004 | Wolf et al. |
| 6,673,603 B2 | 1/2004 | Baetge et al. |
| 6,713,246 B1 | 3/2004 | Reinecke et al. |
| 6,759,188 B2 | 7/2004 | Reinecke et al. |
| 6,777,231 B1 | 8/2004 | Katz et al. |
| 6,790,371 B2 | 9/2004 | Dolocek |
| 6,811,777 B2 | 11/2004 | Mishra |
| 6,875,442 B2 | 4/2005 | Holy et al. |
| 6,905,612 B2 | 6/2005 | Dorian et al. |
| 6,995,013 B2 | 2/2006 | Connelly et al. |
| 7,011,755 B2 | 3/2006 | Sukavaneshvar et al. |
| 7,148,209 B2 | 12/2006 | Hoemann et al. |
| 7,179,391 B2 | 2/2007 | Leach et al. |
| 7,223,346 B2 | 5/2007 | Dorian et al. |
| 7,226,587 B2 | 6/2007 | Clancy et al. |
| 7,374,678 B2 | 5/2008 | Leach et al. |
| 7,465,293 B2 | 12/2008 | Reinecke et al. |
| 7,470,371 B2 | 12/2008 | Dorian et al. |
| 7,553,413 B2 | 6/2009 | Dorian et al. |
| 7,608,258 B2 | 10/2009 | Mishra |
| 8,034,014 B2 * | 10/2011 | Higgins et al. ............... 604/4.01 |
| 8,048,321 B2 | 11/2011 | Leach et al. |
| 2001/0009757 A1 | 7/2001 | Bischof et al. |
| 2001/0041792 A1 | 11/2001 | Donda et al. |
| 2001/0053764 A1 | 12/2001 | Sims et al. |
| 2002/0076400 A1 | 6/2002 | Katz et al. |
| 2002/0077276 A1 | 6/2002 | Fredeking |
| 2002/0082220 A1 | 6/2002 | Hoemann et al. |
| 2002/0165582 A1 | 11/2002 | Porter |
| 2002/0182664 A1 | 12/2002 | Dolocek et al. |
| 2003/0050709 A1 | 3/2003 | Noth et al. |
| 2003/0054331 A1 | 3/2003 | Fraser et al. |
| 2003/0082152 A1 | 5/2003 | Hedrick et al. |
| 2003/0171640 A1 | 9/2003 | Canedo |
| 2003/0185803 A1 | 10/2003 | Kadiyala et al. |
| 2003/0191496 A1 | 10/2003 | Edwards et al. |
| 2003/0194397 A1 | 10/2003 | Mishra |
| 2003/0198687 A1 | 10/2003 | Bennett et al. |
| 2003/0205538 A1 | 11/2003 | Dorian et al. |
| 2004/0131601 A1 | 7/2004 | Epstein et al. |
| 2004/0171146 A1 | 9/2004 | Katz et al. |
| 2004/0182788 A1 | 9/2004 | Dorian et al. |
| 2004/0182795 A1 | 9/2004 | Dorian et al. |
| 2004/0210282 A1 | 10/2004 | Flock et al. |
| 2004/0251217 A1 | 12/2004 | Leach et al. |
| 2004/0267333 A1 | 12/2004 | Kronberg |
| 2005/0049640 A1 | 3/2005 | Gurtner et al. |
| 2005/0065394 A1 | 3/2005 | Spiegel |
| 2005/0076396 A1 | 4/2005 | Katz et al. |
| 2005/0084961 A1 | 4/2005 | Hedrick et al. |
| 2005/0084962 A1 | 4/2005 | Simon |
| 2005/0100536 A1 | 5/2005 | Mishra |
| 2005/0109716 A1 | 5/2005 | Leach et al. |
| 2005/0130301 A1 | 6/2005 | McKay et al. |
| 2005/0153441 A1 | 7/2005 | Hedrick et al. |
| 2005/0153442 A1 | 7/2005 | Katz et al. |
| 2005/0186120 A1 | 8/2005 | Dorian et al. |
| 2005/0186193 A1 | 8/2005 | Mishra |
| 2005/0196874 A1 | 9/2005 | Dorian et al. |
| 2005/0205498 A1 | 9/2005 | Sowemimo-Coker et al. |
| 2005/0251257 A1 | 11/2005 | Mitchell et al. |
| 2005/0260174 A1 | 11/2005 | Fraser et al. |
| 2005/0260175 A1 | 11/2005 | Hedrick et al. |
| 2005/0271738 A1 | 12/2005 | Simon |
| 2005/0282275 A1 | 12/2005 | Katz et al. |
| 2005/0288744 A1 | 12/2005 | Pilla et al. |
| 2006/0051865 A1 | 3/2006 | Higgins et al. |
| 2006/0057693 A1 | 3/2006 | Simon |
| 2006/0083720 A1 | 4/2006 | Fraser et al. |
| 2006/0094112 A1 | 5/2006 | Babalola et al. |
| 2006/0175242 A1 | 8/2006 | Dorian et al. |
| 2006/0175244 A1 | 8/2006 | Dorian et al. |
| 2006/0175268 A1 | 8/2006 | Dorian et al. |
| 2006/0243676 A1 | 11/2006 | Swift et al. |
| 2006/0263407 A1 | 11/2006 | Mishra |
| 2006/0273049 A1 | 12/2006 | Leach et al. |
| 2006/0278588 A1 | 12/2006 | Woodell-May |
| 2007/0034579 A1 | 2/2007 | Dorian et al. |
| 2007/0036768 A1 | 2/2007 | Fraser et al. |
| 2007/0042016 A1 * | 2/2007 | Nayak et al. .................. 424/423 |
| 2007/0075016 A1 | 4/2007 | Leach |
| 2007/0092494 A1 | 4/2007 | Higgins et al. |
| 2007/0104694 A1 * | 5/2007 | Quijano et al. .............. 424/93.7 |
| 2007/0105769 A1 | 5/2007 | Simon |
| 2007/0207161 A1 | 9/2007 | Ralph |
| 2007/0208321 A1 | 9/2007 | Leach et al. |
| 2007/0299472 A1 | 12/2007 | Brighton |
| 2008/0011684 A1 | 1/2008 | Dorian et al. |
| 2008/0064626 A1 | 3/2008 | Zanella |
| 2008/0193424 A1 | 8/2008 | McKale et al. |
| 2008/0226604 A9 * | 9/2008 | Kellar et al. .................. 424/93.7 |
| 2008/0268064 A1 | 10/2008 | Woodell-May |
| 2008/0269762 A1 | 10/2008 | Simon et al. |
| 2008/0283474 A1 | 11/2008 | Leach et al. |
| 2009/0014391 A1 | 1/2009 | Leach et al. |
| 2009/0047242 A1 | 2/2009 | Reinecke et al. |
| 2009/0101599 A1 | 4/2009 | Dorian et al. |
| 2009/0112146 A1 | 4/2009 | Wratten et al. |
| 2009/0148486 A1 | 6/2009 | Lu et al. |
| 2009/0181019 A1 | 7/2009 | Solinger |
| 2009/0192528 A1 | 7/2009 | Higgins et al. |
| 2009/0220482 A1 | 9/2009 | Higgins et al. |
| 2009/0221075 A1 | 9/2009 | Dorian et al. |
| 2009/0236297 A1 | 9/2009 | Dorian et al. |
| 2009/0250413 A1 | 10/2009 | Hoeppner |
| 2009/0253566 A1 | 10/2009 | Chavarria |

(56) References Cited

U.S. PATENT DOCUMENTS

| | | | |
|---|---|---|---|
| 2009/0317439 | A1 | 12/2009 | Turzi et al. |
| 2010/0008992 | A1 | 1/2010 | Ichim |
| 2010/0015129 | A1 | 1/2010 | Abramson et al. |
| 2010/0055087 | A1 | 3/2010 | Higgins et al. |
| 2010/0125236 | A1 | 5/2010 | Bare et al. |
| 2011/0059082 | A1 | 3/2011 | Germer et al. |
| 2011/0059083 | A1 | 3/2011 | Aigner et al. |
| 2011/0059084 | A1 | 3/2011 | Osterroth et al. |
| 2011/0189172 | A1 | 8/2011 | Solinger et al. |
| 2011/0268708 | A1 | 11/2011 | Lin et al. |
| 2012/0027746 | A1 | 2/2012 | Dorian et al. |
| 2012/0093936 | A1 | 4/2012 | Lindenberg et al. |

FOREIGN PATENT DOCUMENTS

| | | |
|---|---|---|
| WO | WO 00/53795 | 9/2000 |
| WO | WO 02/35985 | 5/2002 |
| WO | WO 03/040346 | 5/2003 |
| WO | WO 03/053346 | 7/2003 |
| WO | WO 03/053362 | 7/2003 |
| WO | WO 03/080801 | 10/2003 |
| WO | WO 03/088905 | 10/2003 |
| WO | WO 03/092894 | 11/2003 |
| WO | WO 03/099412 | 12/2003 |
| WO | WO 2004/009207 | 1/2004 |
| WO | WO 2005/004886 | 1/2005 |
| WO | WO 2005/034843 | 4/2005 |
| WO | WO 2008/100442 | 8/2008 |
| WO | WO 2012/030593 | 3/2012 |

OTHER PUBLICATIONS

"Stem Cells: A Primer", National Institutes of Health, http://www.nih.gov/news/stemcell/primer.htm, Sep. 2002 (17 pages).
"Use of Electrical and Magnetic Stimulation in Orthopedics and Traumatology", Consensus Conference, Bologna, Jun. 11, 1997 (27 pages).
Aaron et al., "Acceleration of Experimental Endochondral Ossification by Biophysical Stimulation of the Progenitor Cell Pool", Journal of Orthopaedic Research, vol. 14, No. 4, 1996, pp. 582-589.
Aaron et al., "Power Frequency Fields Promote Cell Differentiation Coincident With an Increase in Transforming Growth Factor-β1 Expression", Bioelectromagnetics, vol. 20, 1999, pp. 453-458.
Aaron et al., "Stimulation of Experimental Endochondral Ossification by Low-Energy Pulsing Electromagnetic Fields", Journal of Bone and Mineral Research, vol. 4, No. 2, 1989, pp. 227-233.
Aaron et al., "Therapeutic Effects of Electromagnetic Fields in the Stimulation of Connective Tissue Repair", Journal of Cellular Biochemistry, vol. 52, 1993, pp. 42-46.
Aaron et al., "Upregulation of basal TGFβ1 levels by EMF coincident with chondrogenesis—implications for skeletal repair and tissue engineering", Journal of Orthopaedic Research, vol. 20, 2002, pp. 233-240.
Anitua et al. "Autologous Platelets as a Source of Proteins for Healing and Tissue Regeneration" Thromb Haemost 91: 4-15 (2004).
Badiavas, E.V. et al., Treatment of Chronic Wounds with Bone Marrow-Derived Cells, Arch Dermatol, vol. 139, pp. 510-516 (2003).
Binderman et al., "Stimulation of skeletal-derived cell cultures by different electric field intensities is cell-specific", Biochimica et Biophysica Acta, vol. 844, 1985, pp. 273-279.
Biomet Biologics, Inc. "Marrowstim Concentration System" Brochure (2008) 20 pages.
Biomet Biologics, Inc. "Plasmax Plasma Concentrate" Brochure (2006) 5 pages.
Biomet Biologics, Inc. "Recover Platelet Separation Kit" Product Brochure. May 2006. (20 pages).
Biomet Biologics, Inc. "Vortech concentration system" Product Brochure. Aug. 2005. 16 pages.
Blanton, Matthew W., M.D. "Adipose Stromal Cells and Platelet-Rich Plasma Therapies Demonstrate Beneficial Healing Properties for Wound Healing" Presentation at Indiana University School of Medicine, May 4, 2006. (9 pages).
Bozic et al., "In Vivo Evaluation of Coralline Hydroxyapatite and Direct Current Electrical Stimulation in Lumbar Spinal Fusion", Spine, vol. 24, No. 20, 1999, pp. 2127-2133.
Brain et al., "Childhood Leukemia: Electric and Magnetic Fields as Possible Risk Factors", Environmental Health Perspectives, vol. 111, No. 7, Jun. 2003, pp. 962-970.
Brodke, Darrel et al. "Bone Grafts Prepared With Selective Cell Retention Technology Heal Canine Segmental Defects as Effectively as Autograft" Journal of Orthopaedic Research, May 2006. Pages 857-866.
Bruder, S.P. et al., Growth Kinetics, Self-Renewal, and the Osteogenic Potential of Purified Human Mesenchymal Stem Cells During Extensive Subcultivation and Following Cryopreservation, J Cell Biochem, 64:278-94 (1997).
Cell Factor Technologies, Inc. "GPS II System, Gravitational Platelet Separation System: Accelerating the Body's Natural Healing Process" Brochure (2005) 16 pages.
Cell Factor Technologies, Inc. "GPS Platelet Concentrate System" Brochure (2004) 9 pages.
Cell Factor Technologies, Inc. "GPS System Shoulder Recovery with the GPS Platelet Concentrate System" Brochure (2004) 6 pages.
Cell Factor Technologies, Inc. "Gravitational Platelet Separation System" User Manual (2005) 13 pages.
Ciombor et al., "Influence of Electromagnetic Fields on Endochondral Bone Formation", Journal of Cellular Biochemistry, vol. 52, 1993, pp. 37-41.
Ciombor et al., "Low frequency EMF regulates chondrocyte differentiation and expression of matrix proteins", Journal of Orthopaedic Research, vol. 20, 2002, pp. 40-50.
Dallari, D. et al. "In Vivo Study on the Healing of Bone Defects Treated With Bone Marrow Stromal Cells, Platelet-Rich Plasma, and Freeze-Dried Bone Allografts, Alone and in Combination" Journal of Orthopaedic Research, May 2006. Pages 877-888.
De Ugarte, D.A. et al., Comparison of Multi-Lineage Cells from Human Adipose Tissue and Bone Marrow, Cells Tissues Organs 174:101-109 (2003).
De Ugarte, D.A. et al., Differential expression of stem cell mobilization-associated molecules on multi-lineage cells from adipose tissue and bone marrow, Immunology Letters 89:267-270 (2003).
DelRossi, Anthony et al. "Platelet-Rich Plasma Reduces Postoperative Blood Loss After Cardiopulmonary Bypass" J Thorac Cardiovasc Surg, vol. 100, Feb. 1990. pp. 281-286.
DeUgarte, Daniel A. et al. "Future of Fat as Raw Material for Tissue Regeneration" Ann Plast Surg, vol. 50, 2003. pp. 215-219.
DiMuzio, Paul et al. "Development of a Tissue-Engineered Bypass Graft Seeded with Stem Cells" Vascular, vol. 14, No. 6, 2006. pp. 338-342.
Dragoo, J.L. et al., Tissue-engineered cartilage and bone using stem cells from human infrapatellar fat pads, J Bone Joint Surg (Br), 85-B: 740-7 (2002).
Duran et al., Pulsed Electromagnetic Fields Enhance BMP-2 Induced Differentiation of Mesenchymal Stem Cells to Osteoblasts, Abstract from Mar. 19-22, 2006 Orthopaedic Research Society Meeting (1page).
Eppich et al., "Pulsed electric fields for selection of hematopoietic cells and depletion of tumor cell contaminants", Nature Biotechnology, vol. 18, Aug. 2000, pp. 882-887.
Eppley, et al. "Platelet Quantification and Growth Factor Analysis from Platelet-Rich Plasma: Implications for Wound Healing," Plastic and Reconstructive Surgery, 114(6):1502-1508 (Nov. 2004).
Erickson, G.R. et al., Chondrogenic Potential of Adipose Tissue-Derived Stromal Cells in Vitro and in Vivo, Biochem Biophys Res Comm, 290, 763-69 (2002).
Floryan, K. et al. "Home Study Program: Intraoperative Use of Autologous Platelet-Rich and Platelet-Poor Plasma for Orthopedic Surgery Patients" vol. 80, No. 4 (Oct. 2004) p. 667-674.
Fodor, W. "Tissue engineering and cell based therapies, from the bench to the clinic: The potential to replace, repair and regenerate", Reproductive Biology and Endocrinology, vol. 1 (102), 2003, pp. 1-6.

(56) References Cited

OTHER PUBLICATIONS

France et al., "The Efficacy of Direct Current Stimulation for Lumbar Intertransverse Process Fusions in an Animal Model", Spine, vol. 26, No. 9, 2001, pp. 1002-1007.
Fraser, John K. et al. "Plasticity of Human Adipose Stem Cells Toward Endothelial Cells and Cardiomyocytes" Nature Clinical Practice; vol. 3, Supplement 1, Mar. 2006. pp. 533-537.
Gimble, Jeffrey M. et al. "Adipose-Derived Stem Cells for Regenerative Medicine" Circulation Research, 2007; vol. 100. pp. 1249-1260.
Gomillion, Cheryl T. et al. "Stem Cells and Adipose Tissue Engineering" Biomaterials, vol. 27, 2006. pp. 6052-6063.
Grove, Joanna et al. "Plasticity of Bone Marrow-Derived Stem Cells" Stem Cells, vol. 22, 2004. pp. 487-500.
Guilak, Farshid et al. "Adipose-Derived Adult Stem Cells for Cartilage Tissue Engineering" Biorheology, vol. 41, 2004. pp. 389-399.
Harvest Technologies SmartPRep2 Brochure (2002) 9 pages.
Hatada et al., "Gene correction in hematopoietic progenitor cells by homologous recombination", PNAS, vol. 97, No. 25, Dec. 5, 2000, pp. 13807-13811.
Hattori, Hidemi et al. "Osteogenic Potential of Human Adipose Tissue-Derived Stromal Cells as an Alternative Stem Cell Source" Cells Tissues Organs, vol. 178, 2004. pp. 2-12.
Hom et al. "Promoting Healing with Recombinant Human Platelet-Derived Growth Factor-BB in a Previously Irradiated Problem Wound" Laryngoscope 113:1566-1571 (Sep. 2003).
Hua et al. "Effect of Electromagnetic Fields on Proliferation and Differentiation of Cultured Mouse Bone Marrow Mesenchymal Stem Cells", Journal of Huazhong University of Science and Technology, vol. 25 (2), 2005, pp. 185-187.
Ishida, et al. "Platelet-Rich Plasma with Biodegradable Gelatin Hydrogel Promotes Rabbit Meniscal Tissue Regeneration", 52nd Annual Meeting of the Orthopaedic Research Society Paper No. 1035, 1 page (2006).
Johnstone, B. et al., Autologous Mesenchymal Progenitor Cells in Articular Cartilage Repair, Clinical Orthopaedics and Related Research, No. 367S, pp. S156-S-162 (1999).
Jorgensen, C. et al. "Stem Cells for Repair of Cartilage and Bone: The next challenge in osteoarthritis and rheumatoid arthritis" Annuals of the Rheumatic Diseases, Aug. 2000.
Lohmann et al., "Pulsed electromagnetic fields affect phenotype and connexin 43 protein expression in MLO-Y4 osteocyte-like cells and ROS 17/2.8 osteoblast-like cells", Journal of Orthopaedic Research, vol. 21, 2003, pp. 326-334.
Lu, X et al. "Bone Marrow Mesenchymal Stem Cells: Progress in bone/cartilage defect repair" PubMed Abstract, Jan. 2002.
Lucarelli, E. et al., Platelet-derived growth factors enhance proliferation of human stromal stem cells, Biomaterials 24:3095-3100 (2003).
Marlovits et al. "A New Simplified Technique for Producing Platelet-Rich Plasma: A Short Technical Note" Eur Spine J 13 (Suppl. 1) : S102-S106 (Jun. 2004).
Mironov et al. "What is regenerative medicine? Emergence of applied stem cell and developmental biology", Expert Opin. Biol. Ther., vol. 4 (6), 2004, pp. 773-781.
Mizuno, H. et al., Mesengenic Potential and Future Clinical Perspective of Human Processed Lipoaspirate Cells, J Nippon Med Sch 70(4):300-306 (2003).
Molnar, Amy. "Stem Cells From Muscles can Repair Cartilage" press release. American College of Rheumatology, 2005.
Nafziger et al., "Investigation of the Effects of 50 Hz Magnetic Fields on Purified Human Hematopoietic Progenitors", Life Sciences, vol. 61, No. 19, 1997, pp. 1935-1946.
Nakagami, Hironori et al. "Novel Autologous Cell Therapy in Ischemic Limb Disease Through Growth Factor Secretion by Cultured Adipose Tissue-Derived Stromal Cells" Arterioscler Thromb Vac Biol, vol. 25, 2005. pp. 2542-2547.
Nathan, Suresh et al. "Cell-Based Therapy in the Repair of Osteochondral Defects: A Novel Use for Adipose Tissue" Tissue Engineering, vol. 9, No. 4, 2003. pp. 733-744.
Nixon et al. "Platelet Enriched Plasma Provides an Intensely Anabolic Vehicle for Sustained Chondrocyte Function After Implantation" Paper No. 1416, 52nd Annual Meeting of the Orthopaedic Research Society (Mar. 2006).
Ogawa, R. et al., Osteogenic and chondrogenic differentiation by adipose-derived stem cells harvested from GFP transgenic mice, Biochem Biophys Res Comm 313:871-877 (2004).
Parker, Anna M. et al. "Adipose-Derived Stem Cells for the Regeneration of Damaged Tissues" Expert Opin. Biol. Ther. vol. 6, No. 6, 2006. pp. 567-578.
Ponticiello, Michael S. "A Rapid Technique for the Isolation and Concentration of Stem Cells From Human Bone Marrow". Presented at the Society for Biomaterials Annual Meeting (Apr. 2006). 1 page.
Rigotti, Gino et al. "Clinical Treatment of Radiotherapy Tissue Damage by Lipoaspirate Transplant: A Healing Process Mediated by Adipose-Derived Adult Stem Cells" Plast Reconstr Surg, vol. 119, 2007. pp. 1409-1422.
Rubin, J. Peter et al. "Clincial Treatment of Radiotherapy Tissue Damage by Lipoaspirate Transplant: A Healing Process Mediated by Adipose-Derived Adult Stem Cells" Plast Reconstr Surg, vol. 119, No. 5, 2007. pp. 1423-1424.
Schaffler, Andreas et al. "Concise Review: Adipose Tissue-Derived Stromal Cells—Basic and Clinical Implications for Novel Cell-Based Therapies" Stem Cells, vol. 25, 2007. pp. 818-827.
Swift, Matthew et al. "Efficient Harvest of a Mononuclear Cell-Rich Fraction From Aspirated Bone Marrow". Presented at the 53rd Annual Meeting of the Orthopaedic Research Society (Feb. 11-14, 2007). 2 pages.
Swift, Matthew J. "Characterization of Growth Factors in Platelet Rich Plasma" Cell Factor Technologies, Inc. Printed Sep. 16, 2005 from www.cellfactortech.com/global_products.cfm.
Wikipedia online encyclopedia article "ABO blood group system" accessed Jul. 28, 2009. (http://en.wikipedia.org/wiki/ABO).
Wikipedia online encyclopedia article "Bone" accessed Apr. 21, 2010. (http://en.wikipedia.org/wiki/Bone).
Wikipedia online encyclopedia article "Fibroblast" accessed Apr. 21, 2010. (http://en.wikipedia.org/wiki/Fibroblast).
Wikipedia online encyclopedia article "Haversian canals" accessed Jan. 26, 2010. (http://en.wikipedia.org/wiki/Haversian_canals).
Wikipedia online encyclopedia article "Osteoblast" accessed Apr. 21, 2010. (http://en.wikipedia.org/wiki/Osteoblast).
Wikipedia online encyclopedia article "Osteon" accessed Jan. 26, 2010. (http://en.wikipedia.org/wiki/Osteon).
Wikipedia online encyclopedia article "Trypsin" accessed Jul. 28, 2009. (http://en.wikipedia.org/wiki/Trypsin).
Woodell-May, et al. "Producing Accurate Platelet Counts for Platelet Rich Plasma: Validation of a Hematology Analyzer and Preparation Techniques for Counting," Scientific Foundation, Journal of Craniofacial Surgery 16(5):749-756 (Sep. 2005).
Yoon, Eulsik et al. "In Vivo Osteogenic Potential of Human Adipose-Derived Stem Cells/Poly Lactide-Co-Glycolic Acid Constructs for Bone Regeneration in a Rat Critical-Sized Calvarial Defect Model" Tissue Engineering, vol. 13, No. 3, 2007. pp. 619-627.
Zuk, P.A. et al., Human Adipose Tissue is a Source of Multipotent Stem Cells, Mol Biol Cell, vol. 13, 4279-95 (2002).
Zuk, Patricia A. "Multilineage Cells from Human Adipose Tissue: Implications for Cell-Based Therapies" Tissue Engineering, vol. 7, No. 2, 2001. pp. 211-228.
Bendele et al. "Combination benefit of treatment with the cytokine inhibitors interleukin-1 receptor antagonist and PEGylated soluble tumor necrosis factor receptor type I in animal models of rheumatoid arthritis" Arthritis & Rheumatism, vol. 43, No. 12, Dec. 2000, pp. 2648-2659.
Burnouf, T. "Blood-derived, tissue engineering biomaterials" Biomedical Engineering—Applications, Basis & Communications, vol. 16, No. 6, Dec. 2004 (pp. 294-304).
Kim, Seon Hee et al. "Ex vivo gene delivery of II-1Ra and soluble TNF receptor confers a distal synergistic therapeutic effect in antigen-induced arthritis", Molecular Therapy, vol. 6, No. 5, Nov. 1, 2002 (pp. 591-600).
Morizaki, et al. "The Effects of Platelet-Rich Plasma on Bone Marrow Stromal Cell Transplants for Tendon Healing In Vitro" J Hand Surg Am. Nov. 2010 ; 35(11): 1833-1841. doi:10.1016/j.jhsa.2010.07.034.

\* cited by examiner

ANGIOGENESIS INITIATION AND GROWTH

CROSS-REFERENCE TO RELATED APPLICATIONS

This application is a continuation of U.S. patent application Ser. No. 11/714,520 filed Mar. 6, 2007, the disclosure of which is incorporated herein by reference.

INTRODUCTION

The present technology relates to methods for promoting angiogenesis, including vascularizing an avascular site, or extending or enhancing existing vasculature.

Angiogenesis is generally referred to as the growth of new and/or extension of preexisting blood vessels and is an important natural process in the body. Angiogenesis occurs following an injury as part of normal wound healing to restore blood flow to damaged tissues. Methods and compositions that promote and enhance angiogenesis are desirable and would prove beneficial in treating damaged or diseased tissue.

SUMMARY

The present technology provides a method for promoting angiogenesis at a site on or within a patient. In some embodiments, the method comprises obtaining blood compatible with the patient and isolating platelet-rich plasma by centrifugation of the blood. The platelet-rich plasma is administered to the site, and then the site is stimulated with an electromagnetic field. Angiogenesis is thereby promoted at the site due to application of the platelet-rich plasma and the electromagnetic field.

Further areas of applicability of the present teachings will become apparent from the detailed description provided herein. It should be understood that the detailed description and specific examples, while indicating various embodiments of the teachings, are intended for purposes of illustration only and are not intended to limit the scope of the teachings.

BRIEF DESCRIPTION OF THE DRAWINGS

The present teachings will become more fully understood from the detailed description and the accompanying drawings, wherein.

DESCRIPTION

The description of the following technology is merely exemplary in nature of the subject matter, manufacture, and use of the teaching disclosed herein, and is not intended to limit the scope, application, or uses of any specific invention claimed in this application, or in such other applications as may be filed claiming priority to this application, or patents issuing therefrom.

Figure 1:
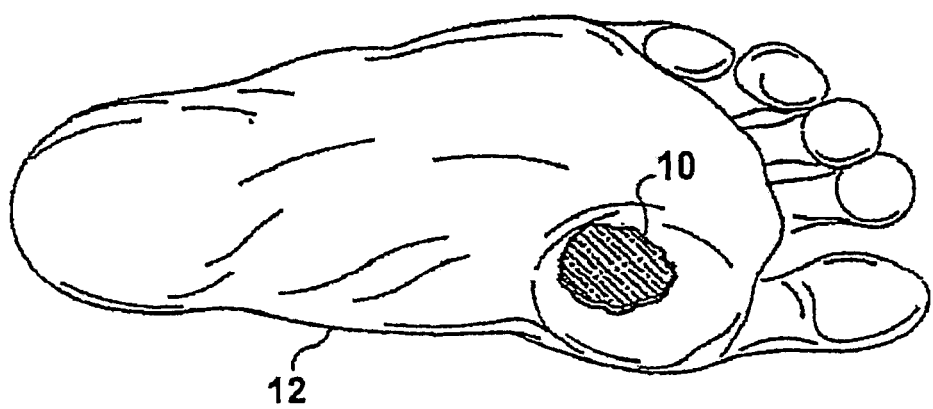
FIG. 1 illustrates a representative site on a patient in which the promotion of angiogenesis is desirable according to one embodiment of the present teachings.

Referring to FIG. 1, a soft tissue wound 10 on a patient's foot 12 is shown. The soft tissue wound may be an ulcer (e.g., a venous ulcer, pressure ulcer, or diabetic ulcer), and it may be located on a body extremity or elsewhere on a patient's body, such as on the torso or head. While the following discussion uses a soft tissue wound on a foot as a representative example of a site on a patient where angiogenesis is desired, other suitable locations and conditions exist. Some examples of sites where promoting angiogenesis is beneficial include locations exhibiting the following conditions: coronary artery disease, stroke, delayed wound healing, chronic wounds, peripheral vascular disease, ischemia, chronic tendonosis, wounds or tissue breakdown resulting from radiation treatment, and myocardial infarction.

Figure 2:
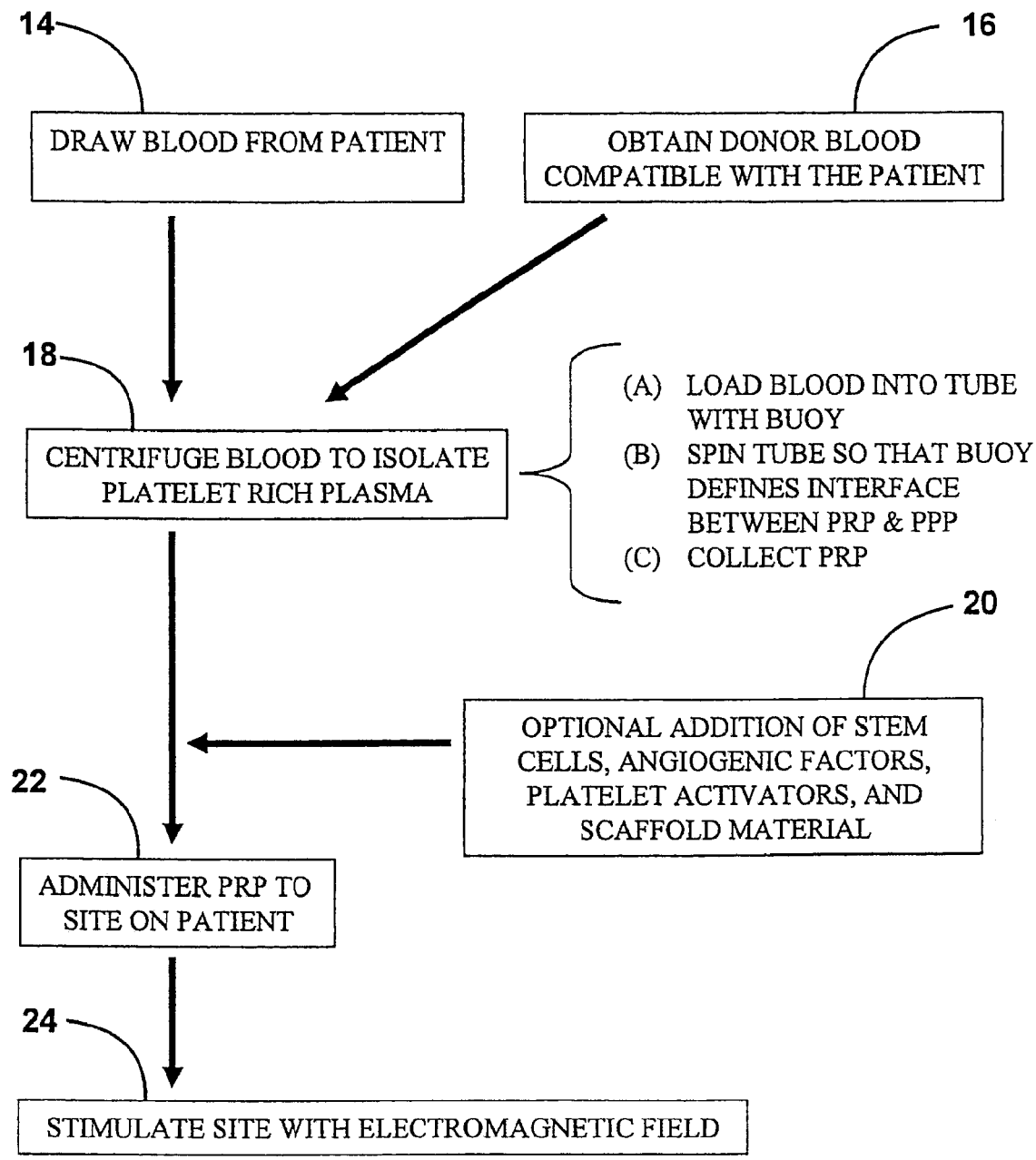
FIG. 2 is a schematic illustration of a representative method for promoting angiogenesis according to one embodiment of the present teachings.

One embodiment of the method for promoting angiogenesis is shown diagrammatically in FIG. 2. In summary, blood may be initially drawn from the patient at step 14. Alternatively, donor blood identified as compatible with the patient may be obtained as shown by step 16. At step 18, platelet-rich plasma is isolated from the blood of the patient and/or the blood donor. After the platelet-rich plasma has been isolated at step 18, optional materials, such as stem cells, angiogenic factors, platelet activators, and scaffold materials, may be added at step 20. Platelet-rich plasma, with one or more optional materials if desired, is then administered to the site at step 22, and then the site is stimulated with an electromagnetic field at step 24. The platelet-rich plasma and the electromagnetic stimulation act in concert to more effectively promote angiogenesis at the site than when the components are used individually. In this regard, administration of platelet-rich plasma, together with stimulating the site with an electromagnetic field, results in more complete vascularization and/or re-vascularization of the site compared to vascularization achieved using either step alone. Each of the steps identified above will be more fully discussed below.

As discussed above, blood compatible with the patient is initially obtained so that platelet-rich plasma may be isolated. This can include drawing the patient's own blood as indicated by step 14 and/or obtaining donor blood compatible with the patient as indicated by step 16. Blood from the patient can be obtained as needed or can be obtained hours, days, or several weeks in advance of the treatment, based on blood storage and preservation methods as generally practiced in the art. If donor blood is to be used, compatible donor blood can be identified using standard blood tests, including, for example, matching blood cell surface antigens.

Figure 3:
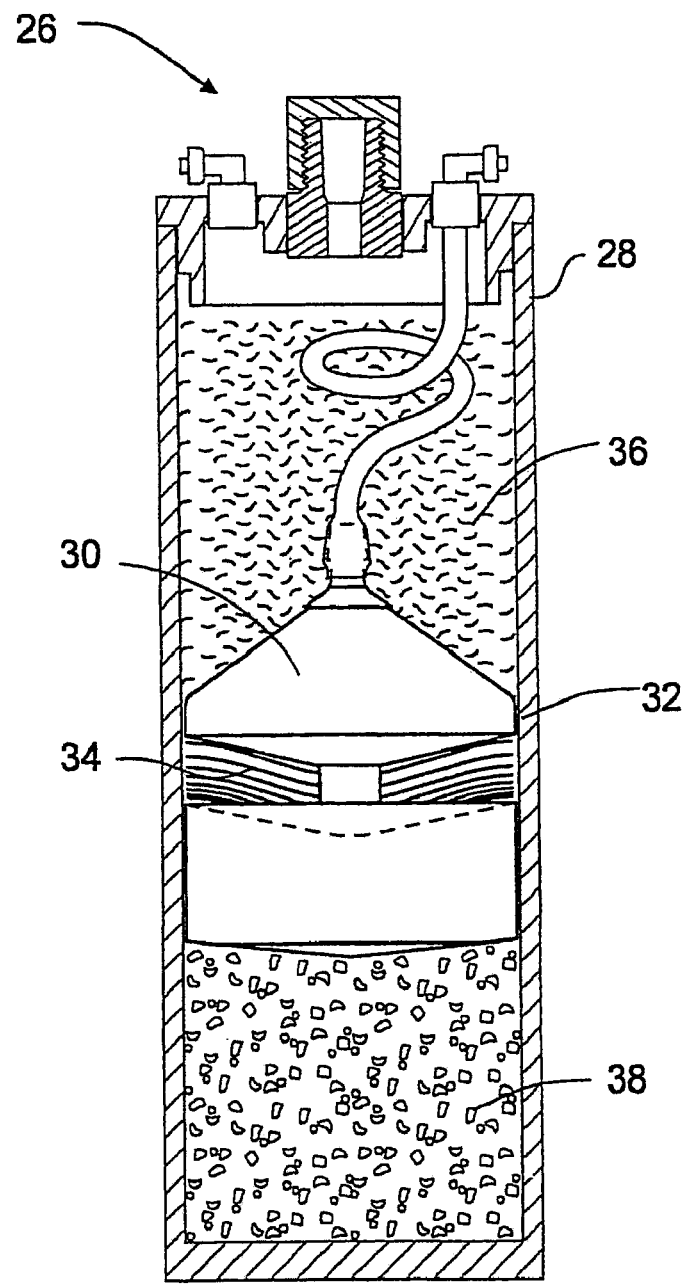
FIG. 3 is a cross-sectional view of a representative device used for isolating platelet-rich plasma according to one embodiment of the present teachings.

Once blood is obtained from the patient at step 14 and/or from a donor at step 16, platelet-rich plasma is isolated at step 18. Platelet-rich plasma can be isolated from the blood obtained in steps 14 or 16 by one or more techniques including filtration, and density fractionation methods such as centrifugation of whole blood, centrifugation of blood in multiple stages, and continuous-flow centrifugation. One example of a device that may be used in isolating platelet-rich plasma is shown in FIG. 3. In this regard, blood obtained in either steps 14 or 16 is initially loaded into the device 26 having a tube 28 with a buoy 30 located within the tube 28. The device 26 is then centrifuged so that the buoy 30 defines an interface 32 between platelet-rich plasma 34 and platelet poor plasma 36. The remaining red blood cells 38 sediment below the buoy 30. Once the platelet-rich plasma 34 has been isolated by the buoy 30 during centrifugation, the platelet-rich plasma 34 can be collected and applied to the patient as discussed below.

Embodiments of such devices used for isolating platelet-rich plasma include the GPS® II Platelet Concentrate Separation Kit and the Plasmax™ Plus Plasma Concentrator accessory (Biomet Biologics, Inc., Warsaw, Ind.). Such devices and methods are described in U.S. Patent Application Publication 2004/0251217 (Leach et al.), and U.S. Patent Application Publication 2005/0109716 (Leach et al.), which are hereby incorporated by reference.

Another example of a device that may be used in isolating platelet-rich plasma by density fractionation includes a centrifugal drum separator and an erythorocyte capture trap. In one embodiment, the walls of the centrifugal drum separator are coated with a depth filter having pores and passageways that are sized to receive and entrap erythrocytes. Blood is placed in the centrifugal drum, and the drum is spun along its axis at sufficient speed so as to force erythrocytes from the blood into the depth filter. After spinning, the erythrocytes remain in the filter and the remaining platelet-rich plasma is extracted. The platelet-rich plasma may be concentrated by desiccation. Embodiments of such devices include the Vortech™ Concentration System (Biomet Biologics, Inc., Warsaw, Ind.), and are disclosed in U.S. Patent Application Publication 2006/0175244 (Dorian et al.) and U.S. Patent Application Publication 2006/0175242 (Dorian et al.), which are hereby incorporated by reference. Such devices may be used to prepare platelet-rich plasma in lieu of or in addition to using the tube having a buoy that is described above and shown in FIG. 2.

Other devices for isolating platelet-rich plasma use high speed centrifugation to pellet the platelets and red blood cells. The pelleted platelets are then resuspended using some of the plasma supernatant or another suitable solution. It will be understood, however, that other suitable methods for forming the platelet-rich plasma 34 may also be used.

The concentration of platelets within the platelet-rich plasma 34 may vary. For example, in some embodiments, the platelet concentration in the platelet-rich plasma 34 can be from about 3-fold to about 10-fold greater than the platelet concentration in whole blood. Furthermore, the platelet-rich plasma 34 can contain cytokines, growth factors, and other proteins and molecules in addition to those contained within or fractionating with the platelets. For example, pelleted platelets that are resuspended in whole or in part with a plasma supernatant can contain cytokines and growth factors from the plasma supernatant.

Referring again to FIG. 2, optional materials, such as stem cells, angiogenic factors, platelet activators, and scaffold materials, may be used with the platelet-rich plasma 34 as indicated by step 20. With respect to the use of stem cells, the source of the stem cells may be adipose stromal cells and/or stem cells derived from bone marrow aspirate. The stem cells can be mammalian stem cells, and in various embodiments, are human stem cells. Adipose stromal cells may be derived from adult adipose tissue harvested by lipoaspiration or liposuction. Such methods include those disclosed in U.S. Pat. No. 6,355,239 and U.S. Pat. No. 6,541,024. Stem cells derived from bone marrow aspirate can be harvested by needle aspiration of bone marrow and may be harvested from the posterior illiac crest, anterior illiac crest, sternum or tibia. The stem cells may be autologous cells, allogenic cells, or xenogeneic cells. Preferably, the stem cells are autologous or allogenic. Stem cells can be applied to the site just prior to the administration of the platelet-rich plasma 34, concomitant with administration the platelet-rich plasma 34, or following administration of the platelet-rich plasma 34 to the patient.

In some embodiments, isolation of stem cells can be performed by extraction of tissue by standard lipoaspiration, isolation from excised adipose tissue, or by using the VASER® ultrasound disruptor in combination with the VENTX™ cannula, available from Sound Surgical Technologies, LLC, Louisville, Colo. The GPS™ biomaterial separation unit (Biomet Biologics, Inc., Warsaw, Ind.) can also be used to isolate adipose stem cells from aspirated adipose tissue. Such devices and methods are described in U.S. Patent Application Publication 2004/0251217 and U.S. Patent Application Publication 2005/0109716 which are hereby incorporated by reference.

Step 20 may also involve the addition or use of platelet activators. The platelet activators serve to release the growth factors within the platelets forming the platelet-rich plasma 34. Platelet activators may include thrombin, calcium chloride, collagen, and mixtures thereof. Activation of the platelets in platelet-rich plasma 34 by the platelet activators can occur just prior to administration of the platelet-rich plasma 34 to the patient, concomitant with administration the platelet-rich plasma 34 to the patient, or following administration of the platelet-rich plasma 34 to the patient.

Step 20 can also involve the use of various angiogenic factors. Angiogenic factors can include, but are not limited to, the following molecules: angiogenin, angiopoietin-1, del-1 protein, fibroblast growth factors such as acidic FGF (also known as aFGF or FGF-1) and basic FGF (also known as bFGF or FGF-2), follistatin, granulocyte colony-stimulating factor (G-CSF), hepatocyte growth factor (HGF), interleukin-8 (IL-8), leptin, midkine, placental growth factor, platelet-derived endothelial growth factor (PD-ECGF), platelet-derived growth factor (PDGF), pleiotrophin (PTN), progranulin, proliferin, transforming growth factor alpha (TGF-α), transforming growth factor beta (TGF-β), tumor necrosis factor alpha (TNF-α), vascular endothelial growth factor (VEGF), and vascular permeability factor (VPF). In various embodiments, isolated, recombinant, and/or synthetic angiogenic factors may be used. Angiogenic factors can be applied to the site just prior to the administration of the platelet-rich plasma 34, concomitant with administration the platelet-rich plasma 34, or following administration of the platelet-rich plasma 34 to the patient.

A scaffold may be included as indicated at step 20 to contain, support, or retain the platelet-rich plasma or other materials used in the present methods at the tissue defect site. For example, a scaffold may contain or support stem cells that may be included in step 20, preferably enabling growth and/or retention of the stem cells at the site of implantation. The scaffold may also provide a support for retention of the platelet-rich plasma at the wound site. In addition, the scaffold may facilitate migration of endogenous cells into the administration site. The scaffold may be implanted or applied at the tissue defect site, followed by the administration of platelet-rich plasma and optional materials in step 22. Alternatively, the platelet-rich plasma or optional material may be combined with the scaffold prior to administration in step 22.

Scaffolds may be formed from porous or semi-porous, natural, synthetic or semisynthetic materials. In some wound treatment applications, a scaffold material can be an osteoconductive material. Scaffold materials include those selected from the group consisting of bone (including cortical and cancellous bone), demineralized bone, ceramics, polymers, and combinations thereof. Suitable polymers may include collagen, including lyophilized or skin-derived collagen as disclosed in U.S. patent application Ser. No. 11/259,216 which is hereby incorporated by reference. Polymers may also include, gelatin, hyaluronic acid, chitosan, polyglycolic acid, polylactic acid, polypropylenefumarate, polyethylene glycol, and copolymers or combinations thereof.

Ceramics include any of a variety of ceramic materials known in the art for use for implanting in bone, such as calcium phosphate (including tricalcium phosphate, tetracalcium phosphate, hydroxyapatite, and mixtures thereof). Ceramics useful herein include those described in U.S. Pat. No. 6,323, 146 and U.S. Pat. No. 6,585,992. A commercially available ceramic is ProOsteon™ from Interpore Cross International, Inc. (Irvine, Calif.).

After the platelet-rich plasma 34 has been isolated at step 18, it is administered to the site of a tissue defect in step 22, optionally with one or more optional materials such as platelet activators, stem cells, angiogenic factors, buffering agents and scaffold materials as may be added in step 20. When such optional materials are used, the platelet-rich plasma 34 and one or more optional materials can be administered either together as a single composition, or the platelet-rich plasma and each material can be administered separately or in various sub-combinations.

Figure 4:
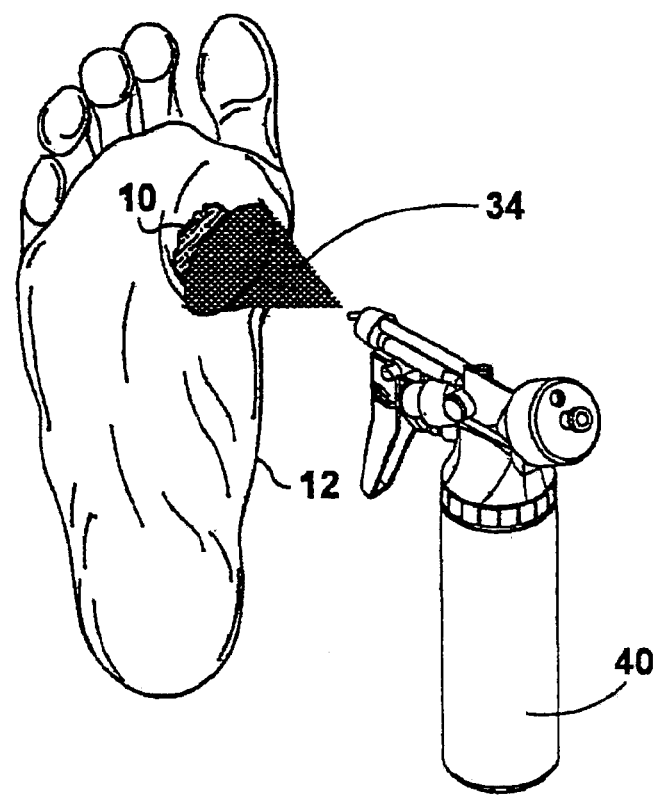
FIG. 4 illustrates a representative manner of administrating platelet-rich plasma to the patient according to one embodiment of the present teachings.

In certain forms of treatment, the platelet-rich plasma 34 may be applied to an external surface of the patient. For example, as shown in FIG. 4, the platelet-rich plasma 34 can be sprayed onto the site of a skin wound 10 using a spray applicator 40 containing the platelet-rich plasma 34.

In other forms of treatment, the platelet-rich plasma 34 may be applied at a site internal to the patient. In this regard, platelet-rich plasma 34 can be injected into internal tissue or organs by means of a syringe. In addition, platelet-rich plasma 34 can be administered in conjunction with a surgical procedure. The administration of the platelet-rich plasma 34 to an site internal to the patient can be used to treat, for example, the effects of coronary artery disease, stroke, delayed wound healing, chronic wounds, peripheral vascular disease, ischemia, chronic tendonosis, wounds or tissue breakdown resulting from radiation treatment, and myocardial infarction. It should be understood, however, that the step of administering platelet-rich plasma 34 may also comprise any biomedically acceptable process or procedure by which the platelet-rich plasma 34 is implanted, injected, or otherwise administered in, on, or in proximity to the site on a patient so as to have a beneficial effect by promoting angiogenesis.

Figure 5:
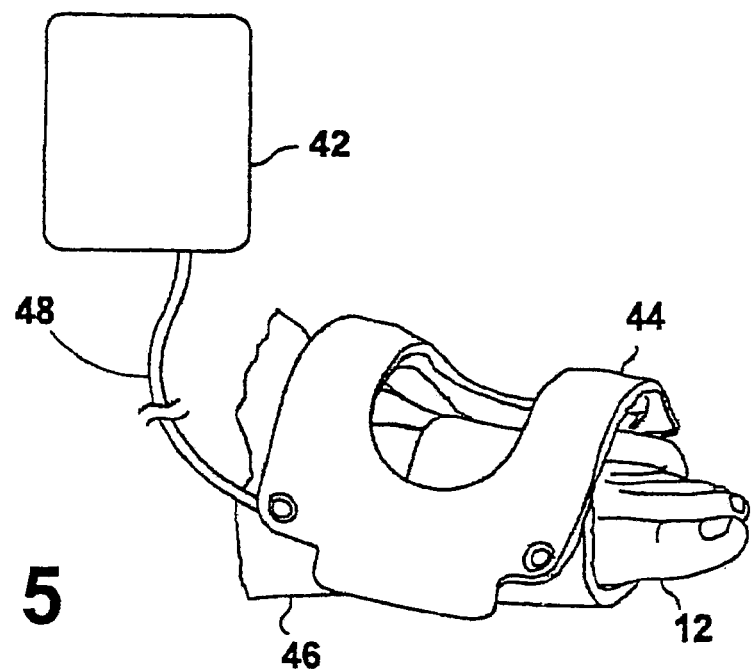
FIG. 5 illustrates a representative manner for stimulating the site on the patient with an electromagnetic field according to one embodiment of the present teachings.

Following the application of platelet-rich plasma 34 to the site at step 22, the site is stimulated with an electromagnetic field as indicated by step 24. Stimulating the site with an electromagnetic field may involve various forms of electromagnetic stimulation. In one embodiment illustrated in FIG. 5, the site is stimulated using a power source 42 coupled to a stimulation coil 44. The current passing through the coil produces a pulsing magnetic field which induces in the site to be treated a pulsing electric field. The coil 44 may be a saddle-shaped coil that at least partially surrounds a wound site on the patient's foot 12 and the adjacent tissue, and it may be held in place with a bandage, tape, Velcro® or other suitable fasteners, or as part of a padded boot 46. The coil 44 is connected via a cable 48 to the power source 42 which may be held against the patient's body (e.g., on the thigh or on the waist) in any suitable manner.

Step 24 involving the stimulation of a site with an electromagnetic field may also include placing at least two electrodes across the site to be treated on the patient. Electrical energy may then be applied to the electrodes so as to capacitively couple the electrodes and generate the electromagnetic field therebetween. The electromagnetic field is therefore able to pass through the platelet-rich plasma 34 so as to promote angiogenesis at the site by upregulation of angiogenic factors, including FGF-2, and extension of preexisting and/or growth of new blood vessels. In other embodiments, step 24 may also involve implanting electrodes to produce a direct current, or one or more coils, into the patient and administering an electric stimulation to the site via the implanted electrodes or coil(s).

The strength of the electromagnetic field produced in the tissue during electrical stimulation is preferably at least about 0.5 microvolts per centimeter whether produced by direct current, capacitive coupled current or pulsed electromagnetic fields. In the case of an implanted direct current electrode, the amplitude of the current should be from about 1 to about 200 microamperes in some embodiments, and in other embodiments, the amplitude may be from about 20 to about 100 microamperes. In still further embodiments, the current may be about 20, about 60, or about 100 microamperes. It should be understood, however, that the amplitude of the current may be of other suitable magnitudes.

The electromagnetic field applied at step 24 may be constant or vary over time as discussed above. For example, a sinusoidal time varying electromagnetic field can be applied by the electrodes placed across the site. Such a sinusoidal time varying electromagnetic field can have a peak voltage across the electrodes from about 1 volt to about 10 volts, and in some embodiments, the peak voltage can be about 5 volts. The corresponding electric field produced in the tissue can have an amplitude of from about 0.1 millivolt per centimeter (mV/cm) to about 100 mV/cm, and in some embodiments can be about 20 mV/cm. The sinusoidal time varying electric field may have a frequency of from about 1,000 Hz to about 200, 000 Hz, and in some embodiments the frequency may be about 60,000 Hz.

The electromagnetic field applied to the site at step 24 may also be a pulsed electromagnetic field. In this regard, a pulsed electromagnetic field may have a pulse duration of from about 10 microseconds per pulse to about 2000 microseconds per pulse. In addition, the pulse duration of the pulsed electromagnetic field in one embodiment can be about 225 microseconds. The pulses may include in electromagnetic "bursts", in which a burst can comprise from 1 pulse to about 200 pulses. Alternatively, the electromagnetic field may have bursts that comprise from about 10 pulses to about 30 pulses. In this regard, in one embodiment each burst may comprise about 20 pulses.

The frequency at which bursts in the pulsed electromagnetic are applied may vary. In this regard, bursts can be repeated at a frequency of from about 1 Hz to about 100 Hz in some embodiments, and can be repeated at a frequency of about 10 Hz to about 20 Hz in other embodiments. Further, bursts can repeat at a frequency of about 1.5 Hz, about 15 Hz or about 76 Hz. A burst can have a duration from about 10 microseconds up to about 40,000 microseconds. In this regard, a burst can have a duration of about 4.5 milliseconds.

Suitable devices for generating a capacitively coupled electromagnetic field include SpinalPak® spinal stimulator (EBI, L.P., Parsippany, N.J.) or a DC stimulation device such as an SpF® XL IIb spinal fusion stimulator (EBI, L.P., Parsippany, N.J.). Pulsed electromagnetic fields can be produced using various known methods and apparatuses, such as using a single coil or a pair of Helmholtz coils. For example, a suitable apparatus includes the EBI Bone Healing System® Model 2001 (EBI, L.P., Parsippany, New Jersey). With respect to electrical stimulation of internal sites in a patient, a direct current electric field may be generated using any known device for generating a direct current electric field, such as for example, the Osteogen™ implantable bone growth stimulator (EBI, L.P., Parsippany, N.J.). Other suitable devices for generating electromagnetic fields may be used.

Electromagnetic stimulation of the site at step 24 can be continued and/or repeated as necessary after the platelet-rich plasma 34 (and/or the various compositions described herein) has been applied to the patient. It should be understood, however, that the step of stimulating the site with an electromagnetic field includes fields other than, or in addition to, electric or electromagnetic fields associated with ambient conditions (such the electromagnetic fields generated by casual exposure to radios, telephones, desktop computers or similar devices).

Specific examples are provided for illustrative purposes of how to make and use the compositions and methods of this technology and, unless explicitly stated otherwise, are not intended to be a representation that given embodiments of this technology have, or have not, been made or tested.

Example 1

A patient presenting a chronic wound is treated using a method of the present technology. Platelet-rich plasma is prepared from a patient's blood using the GPS® II Platelet Concentrate Separation Kit and the Plasmax™ Plus Plasma Concentrator accessory (Biomet Biologics, Inc., Warsaw, Ind.). Adipose stromal cells are harvested from the patient by performing lipoaspiration to obtain adipose tissue. The adipose tissue is enzymatically digested in collagenase type I solution (Worthington Biochemical) under gentle agitation for 1 hour at 37° C., the dissociated cells are filtered with 500-μm and 250-μm Nitex filters, and centrifuged at 200 g for 5 minutes to separate the stromal cell fraction (pellet) from the adipocytes. The platelet-rich plasma is combined with the isolated adipose stromal cells.

The platelet-rich plasma and adipose stromal cells are administered to the patient's chronic wound site. Electric stimulation in the form of a pulsed electromagnetic field is applied across the site using a stimulation coil. The pulse duration of the pulsed electromagnetic field is about 225 microseconds per pulse. The pulses are comprised of electromagnetic bursts in which each burst contains about 20 pulses. Each burst is repeated at a frequency of about 15 Hertz and has a duration of about 4.5 milliseconds. The platelet-rich plasma, stem cells, and electric stimulation promote angiogenesis and achieve more complete healing of the patient's chronic wound by enhancing vascularization of the site in comparison with a similar wound left untreated.

Example 2

Tissue damaged by chronic ischemia due to peripheral artery occlusive disease is treated by a method of the present disclosure. A composition of platelet-rich plasma is injected to the ischemic site followed by electromagnetic stimulation using direct current.

Allogenic platelets are purified from donated whole blood by high speed centrifugation to sediment the platelets from the plasma. Pelleted platelets are resuspended using a fraction of the plasma supernatant to form a viscous composition of platelet-rich plasma containing about eight times greater concentration of platelets compared to whole blood. The platelet composition is administered to the ischemic site and electromagnetic stimulation is provided across the site using temporarily implanted electrodes. The method promotes angiogenesis and results in revascularization of the ischemic site.

Example 3

A process for promoting angiogenesis is used to promote angiogenesis in a patient's hand exhibiting chronic tendonosis. Blood is drawn from the patient and platelet-rich plasma is isolated from the blood by centrifugation and collection of the buffy coat fraction.

The platelet-rich plasma is administered to the site of the tendonosis by injection and the site is subjected to electromagnetic stimulation comprising a pulsed electromagnetic field by using a pair of Helmholtz coils. The composition promotes angiogenesis where new blood vessels form to supply oxygenated blood to the site.

Example 4

A method for treating a patient with unilateral ischaemia of the leg includes injection of platelet-rich plasma and stem cells derived from bone marrow aspirate (BMA). Blood is drawn from the patient and platelet-rich plasma is isolated using the GPS® II Platelet Concentrate Separation Kit (Biomet Biologics, Inc., Warsaw, Ind.). BMA is harvested from the patient using standard techniques. Stem cells derived from the BMA are concentrated and isolated by centrifugation using the GPS® II device. Both the platelet-rich plasma and the stem cells are isolated and combined in the presence of a citrate-based anticoagulant.

The platelet-rich plasma and the stem cells derived from BMA are administered to the patient around the site of vascular occlusion using intramuscular injection. Between about $1\times10^9$ and about $3\times10^9$ stem cells derived from BMA are combined with platelet-rich plasma in a total volume of about 30 mL. About 0.75 mL of is administered to 40 injection sites in a 3×3 cm grid using a 26-gauge needle at a depth of about 1.5 cm.

Electric stimulation in the form of a pulsed electromagnetic field is applied to the site using a stimulation coil. The pulse duration of the pulsed electromagnetic field is about 225 microseconds per pulse. The pulses are comprised of electromagnetic bursts in which each burst contains about 20 pulses. Each burst is repeated at a frequency of about 15 Hertz and has a duration of about 4.5 milliseconds. The platelet-rich plasma, stem cells derived from BMA, and electric stimulation promote angiogenesis at the site and increase the pain-free walking time of the patient.

The examples and other embodiments described herein are exemplary and not intended to be limiting in describing the full scope of compositions and methods of this technology. Equivalent changes, modifications and variations of specific embodiments, materials, compositions and methods may be made within the scope of the present technology, with substantially similar results.

What is claimed is:

1. A method for promoting angiogenesis at a site on a patient, the method comprising:
    obtaining blood compatible with the patient;
    isolating platelet-rich plasma by density fractionation of said blood;
    administering said platelet-rich plasma to the site; and
    stimulating the site with an electromagnetic field following administration of said platelet-rich plasma to the site, thereby
    promoting angiogenesis at the site upon application of said electromagnetic field and said platelet-rich plasma to the site.

2. The method for promoting angiogenesis at a site on a patient as set forth in claim 1, wherein isolating platelet-rich plasma by density fractionation comprises centrifuging of said blood by:

loading said blood into a tube having a buoy;
spinning said tube so that said buoy defines an interface between platelet-rich plasma and platelet poor plasma contained within said blood; and
collecting said platelet-rich plasma.

3. The method for promoting angiogenesis at a site on a patient as set forth in claim 1, wherein stimulating the site with the electromagnetic field following the administration of said platelet-rich plasma includes generating in the tissue a capacitively coupled time varying electromagnetic field having a peak amplitude of from about 0.1 to about 100 millivolts per centimeter, and having a frequency from about 1 kHz to about 200 kHz.

4. The method for promoting angiogenesis at the site on a patient as set forth in claim 1, wherein stimulating the site with an electromagnetic field following the administration of said platelet-rich plasma includes generating a pulsed electromagnetic field having a pulse duration from about 10 to 2000 microseconds.

5. The method for promoting angiogenesis at a site on a patient as set forth in claim 1, wherein promoting angiogenesis of the site upon application of said electromagnetic field and said platelet-rich plasma comprises:
promoting the production of FGF-2 at the site upon the application of said electromagnetic field; and
upregulating the proliferation of endothelial cells at the site upon application of said electromagnetic field.

6. The method for promoting angiogenesis at a site on a patient as set forth in claim 1, further comprising administering stem cells to the site, said stem cells selected from the group consisting of adipose stromal cells, stem cells derived from bone marrow aspirate, and combinations thereof.

7. The method for promoting angiogenesis at a site on a patient as set forth in claim 6, wherein administering stem cells to the site comprises:
performing lipoaspiration on the patient to obtain adipose tissue, said adipose tissue including adipose stem cells and adipocytes;
enzymatically digesting said adipose tissue; and
separating said adipose stem cells from said adipocytes in said enzymatically digested adipose tissue.

8. The method for promoting angiogenesis at a site on a patient as set forth in claim 6, wherein administering stem cells to the site comprises:
isolating bone marrow aspirate from the patient, said bone marrow aspirate including stem cells;
centrifuging said bone marrow aspirate to concentrate said stem cells;
isolating said concentrated stem cells derived from bone marrow aspirate.

9. The method for promoting angiogenesis at a site on a patient as set forth in claim 1, wherein administering platelet-rich plasma to the site further comprises administering an isolated angiogenic factor selected from the group consisting of angiogenin, angiopoietin-1, del-1 protein, acidic fibroblast growth factor (aFGF or FGF-1), basic fibroblast growth factor (bFGF or FGF-2), follistatin, granulocyte colony-stimulating factor (G-CSF), hepatocyte growth factor (HGF), interleukin-8 (IL-8), leptin, midkine, placental growth factor, platelet-derived endothelial growth factor (PD-ECGF), platelet-derived growth factor (PDGF), pleiotrophin (PTN), progranulin, proliferin, transforming growth factor alpha (TGF-α), transforming growth factor beta (TGF-β), tumor necrosis factor alpha (TNF-α), vascular endothelial growth factor (VEGF), vascular permeability factor (VPF), and combinations thereof.

10. The method for promoting angiogenesis at a site on a patient as set forth in claim 1, wherein the site on the patient exhibits one of the following conditions: coronary artery disease, stroke, delayed wound healing, chronic wound, peripheral vascular disease, ischemia, chronic tendonosis, wound or tissue breakdown resulting from radiation treatment, and myocardial infarction.

11. The method for promoting angiogenesis at a site on a patient as set forth in claim 1, wherein the site on the patient exhibits one of the following conditions: stroke, peripheral vascular disease, ischemia, and wound or tissue breakdown resulting from radiation treatment.

12. A method for promoting angiogenesis at the site of an ulcer on a patient comprising:
obtaining blood compatible with the patient;
isolating platelet-rich plasma by loading said blood into a tube having a buoy, spinning said tube so that said buoy defines an interface between platelet-rich plasma and platelet-poor plasma contained within said blood, and collecting said platelet-rich plasma;
administering said platelet-rich plasma to the site of the ulcer; and
stimulating the site with an electromagnetic field following administration of said platelet-rich plasma to the site, thereby
promoting angiogenesis at the site upon application of said electromagnetic field and said platelet-rich plasma to the site.

13. The method for promoting angiogenesis at a site on a patient as set forth in claim 12, wherein stimulating the site with the electromagnetic field following the administration of said platelet-rich plasma includes generating in the tissue a capacitively coupled time varying electromagnetic field having a peak amplitude of from about 0.1 to about 100 millivolts per centimeter, and having a frequency from about 1 kHz to about 200 kHz.

14. The method for promoting angiogenesis at the site on a patient as set forth in claim 12, wherein stimulating the site with an electromagnetic field following the administration of said platelet-rich plasma includes generating a pulsed electromagnetic field having a pulse duration from about 10 to 2000 microseconds.

15. The method for promoting angiogenesis at a site on a patient as set forth in claim 12, further comprising administering stem cells to the site, wherein said stem cells are selected from the group consisting of adipose stromal cells, stem cells derived from bone marrow aspirate, and combinations thereof.

16. The method for promoting angiogenesis at a site on a patient as set forth in claim 15, wherein administering stem cells to the site comprises:
isolating bone marrow aspirate from the patient, said bone marrow aspirate including stem cells;
centrifuging said bone marrow aspirate to concentrate said stem cells;
isolating said concentrated stem cells derived from bone marrow aspirate.

17. The method for promoting angiogenesis at a site on a patient as set forth in claim 12, wherein administering platelet-rich plasma to the site further comprises administering an isolated angiogenic factor selected from the group consisting of angiogenin, angiopoietin-1, del-1 protein, acidic fibroblast growth factor (aFGF or FGF-1), basic fibroblast growth factor (bFGF or FGF-2), follistatin, granulocyte colony-stimulating factor (G-CSF), hepatocyte growth factor (HGF), interleukin-8 (IL-8), leptin, midkine, placental growth factor, platelet-derived endothelial growth factor (PD-ECGF), platelet-derived growth factor (PDGF), pleiotrophin (PTN), progranulin, proliferin, transforming growth factor alpha (TGF-α), transforming growth factor beta (TGF-β), tumor necrosis factor alpha (TNF-α), vascular endothelial growth factor (VEGF), vascular permeability factor (VPF), and combinations thereof.

18. A method for promoting angiogenesis at the site of a tissue defect in a patient, comprising:
   obtaining blood compatible with the patient;
   isolating platelet-rich plasma by loading said blood with a tube having a buoy, spinning said tube so that said buoy defines an interface between platelet-rich plasma and platelet-poor plasma contained within said blood, and collecting said platelet-rich plasma;
   administering said platelet-rich plasma to the site; and
   stimulating the site with an electromagnetic field following administration of said platelet-rich plasma to the site, thereby
   promoting angiogenesis at the site upon application of said electromagnetic field and said platelet-rich plasma to the site;
   wherein said tissue defect is stroke, peripheral vascular disease, ischemia, or wound or tissue breakdown resulting from radiation treatment.

19. The method for promoting angiogenesis at a site on a patient as set forth in claim 18, wherein stimulating the site with the electromagnetic field following the administration of said platelet-rich plasma includes generating in the tissue a capacitively coupled time varying electromagnetic field having a peak amplitude of from about 0.1 to about 100 millivolts per centimeter, and having a frequency from about 1 kHz to about 200 kHz.

20. The method for promoting angiogenesis at the site on a patient as set forth in claim 18, wherein stimulating the site with an electromagnetic field following the administration of said platelet-rich plasma includes generating a pulsed electromagnetic field having a pulse duration from about 10 to 2000 microseconds.

21. The method for promoting angiogenesis at a site on a patient as set forth in claim 18, further comprising administering stem cells to the site, wherein said stem cells are selected from the group consisting of adipose stromal cells, stem cells derived from bone marrow aspirate, and combinations thereof.

22. The method for promoting angiogenesis at a site on a patient as set forth in claim 21, wherein administering stem cells to the site comprises:
   isolating bone marrow aspirate from the patient, said bone marrow aspirate including stem cells;
   centrifuging said bone marrow aspirate to concentrate said stem cells;
   isolating said concentrated stem cells derived from bone marrow aspirate.

23. The method for promoting angiogenesis at a site on a patient as set forth in claim 18, wherein administering platelet-rich plasma to the site further comprises administering an isolated angiogenic factor selected from the group consisting of angiogenin, angiopoietin-1, del-1 protein, acidic fibroblast growth factor (aFGF or FGF-1), basic fibroblast growth factor (bFGF or FGF-2), follistatin, granulocyte colony-stimulating factor (GCSF), hepatocyte growth factor (HGF), interleukin-8 (IL-8), leptin, midkine, placental growth factor, platelet-derived endothelial growth factor (PD-ECGF), platelet-derived growth factor (PDGF), pleiotrophin (PTN), progranulin, proliferin, transforming growth factor alpha (TGF-α), transforming growth factor beta (TGF-β), tumor necrosis factor alpha (TNF-α), vascular endothelial growth factor (VEGF), vascular permeability factor (VPF), and combinations thereof.

* * * * *